United States Patent [19]
Miyata et al.

[11] Patent Number: 5,310,749
[45] Date of Patent: May 10, 1994

[54] ANTIPROTOZOAL COMPOSITION CONTAINING A 2-NITROIMIDAZOLE DERIVATIVE AND METHOD THEREOF

[75] Inventors: Yoshiyuki Miyata; Masakazu Sakaguchi; Toshimitsu Suzuki, all of Yokohama; Tsutomu Takeuchi, Tokyo; Seiki Kobayashi, Ichikawa, all of Japan

[73] Assignee: Pola Chemical Industries Inc., Shizuoka, Japan

[21] Appl. No.: 703,839

[22] Filed: May 21, 1991

[51] Int. Cl.$^5$ .............................................. A61K 31/04
[52] U.S. Cl. ..................................................... 514/398
[58] Field of Search ......................... 514/397, 398, 42

[56] References Cited

U.S. PATENT DOCUMENTS 4,241,060 12/1980 Smithen .............................. 424/246
4,515,790 5/1985 Hofheinz ............................. 514/234

FOREIGN PATENT DOCUMENTS 0312858 4/1989 European Pat. Off. .

OTHER PUBLICATIONS

Patent Abstracts of Japan, 2-Nitromidazole Derivative and its, Preparation, vol. 8, (JP-A-59 139 363), 1984.
K. Sasai et al, *Int. J. Radiat. Biol*, 1990, vol. 57, No. 5, pp. 971–980.

*Primary Examiner*—Frederick E. Waddell
*Assistant Examiner*—William R. A. Jarvis
*Attorney, Agent, or Firm*—Oblon, Spivak, McClelland, Maier & Neustadt

[57] ABSTRACT

Disclosed herein is an antiprotozoal composition containing a 2-nitroimidazole derivative as its active component. This drug is especially useful against *Trypanosoma cruzi*. Process for the preparation is also disclosed.

2 Claims, No Drawings

ANTIPROTOZOAL COMPOSITION CONTAINING A 2-NITROIMIDAZOLE DERIVATIVE AND METHOD THEREOF

BACKGROUND OF THE INVENTION i) Field of the Invention

This invention relates to an antiprotozoal composition which is especially effective against Trypanosomatidae and a process for preparing the same.

ii) Background Art

In developing countries especially in South America, high death rate due to diseases caused by protozoa is a big issue. Not only the native people, foreign people sent by other countries to help develop the country are also exposed to danger of getting suffered from such diseases.

Among the diseases caused by protozoa, those caused by *Trypanosoma cruzi* are fatal because currently no effective antiprotozoals are known. Especially in the case of acute infections, it is not rare that the patients die from myocardosis. Meanwhile, tens of millions of people suffer from chronic infectious diseases caused by *Trypanosoma cruzi*. Prevention and treatment of these diseases, therefore, has been given top priority by the WHO.

It is sbelieved that the development of an effective antiprotozoal, especially against *Trypanosoma cruzi* is significant for the mankind welfare.

SUMMARY OF THE INVENTION

A primary object of the invention is to provide an antiprotozoal composition which contains as its active component a 2-nitroimidazole derivative of the following formula (I):

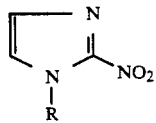

wherein R is —CH$_2$OCH$_2$CH=CHCH$_2$OH, —CH$_2$OCH(CH$_2$OH)$_2$ or

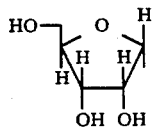

Another object of the invention is to provide an antiprotozoal composition which contains as its active component a 2-nitroimidazole derivative of formula (I):

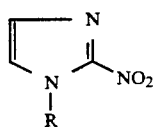

wherein R is —CH$_2$OCH$_2$CH=CHCH$_2$OH, —CH$_2$OCH(CH$_2$OH)$_2$ or

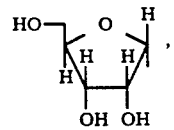

and an anionic polymer.

A further object of the invention is to provide a process for preparing such compositions.

The above and other objects, features and advantages of the present invention will become apparent from the following description.

DETAILED DESCRIPTION OF THE INVENTION AND PREFERRED EMBODIMENTS

The 2-nitroimidazole derivative (I), which is an active component of the antiprotozoal of this invention, is a known compound, and is prepared, for example, by the reaction steps:

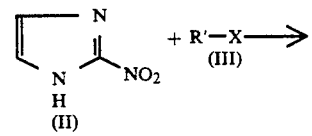

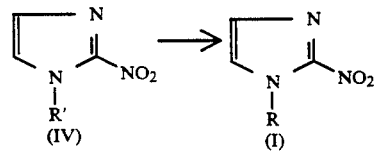

wherein X is a halogen atom, R' is —CH$_2$OCH$_2$CH=CHCH$_2$OAc—CH$_2$OCH(CH$_2$OAc)$_2$ or

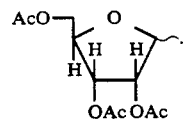

In other words, reaction between 2-nitroimidazole (II) and a halide (III) produces a compound (IV), and deacetylation of the compound (IV) produces the 2-nitroimidazole derivative (I).

The reaction between 2-nitroimidazole (II) and a halide (III) is preferably carried out in the presence of a base such as triethylamine and in a solvent such as dimethylformamide. The deacetylation of compound (IV) is preferably carried out in a mixture solvent of acetonitrile-water in the presence of a base such as triethylamine, pyridine or the like. After completion of the reaction, purification of compound (I) is carried out by condensing the reaction mixture, separating through means such as column chromatography, and then condensing again for recrystalization.

The thus obtained 2-nitroimidazole derivatives (I) have excellent anti-protozoan actions as will hereafter be illustrated in Examples, and are very safe, too. Accordingly, they are useful as a drug against protozoa, namely as an antiprotozoal.

Dosage of the antiprotozoal containing 2-nitroimidazole derivative (I) according to this invention differs depending on the patient's age, sex, weight, administration route, body conditions and the illness. In the case of oral administration, 30 mg-1500 mg/day is suggested and in the case of non-oral administration, 10-500 mg/day is suggested, both for an adult.

Further, the anti-protozoan activity of compound (I) is remarkably enhanced when it is used in combination with an anionic polymer. Especially, it is noted that such combination completely clears up the protozoa from the body of the infected patient, which enables to prevent the symptoms from becoming chronic.

The usable anionic polymers are any of natural origin or synthesized ones. Exemplary natural anionic polymers include mucopolysaccharides such as hyaluronic acid, chondroitin sulfuric acid and their salts; hemicelluloses such as alginic acid, carboxymethylcellulose, hydroxymethylcellulose, hydroxyethylcellulose, hydroxypropylcellulose, hydroxypropylethylcellulose, methylcellulose, carboxymethyl amylose and their salts. Exemplary synthetic anionic polymers include polymers obtained from the polymerization of the following monomers:

(a) Unsaturated carbonic acid monomers such as acrylic acid, methacrylic acid, maleic acid, etc.
(b) Unsaturated sulfonic acid monomers such as styrene sulfonic acid, etc.
(c) Unsaturated phosphoric acid monomers such as vinyl sulfonic acid, acid phosphoxyethyl methacrylate, etc.

Polymers obtained form the copolymerization of the above monomers and other polymerizable monomers may also be used. An example of such copolymer is an acrylic acid-diisobutylvinyl ether copolymer.

The above-mentioned anionic polymers are preferably water-soluble. The proportion of the anionic polymers to compound (I) ranges form 1/1000 to 1/1 on the weight basis.

The antiprotozoal composition of this invention can take various forms. By conventional processes, it is formed into tablets, granule, powder, capsules, suspensions, injections, suppositories, and the like.

In order to make a solid preparation, compound (I) is first blended with pharmaceutically acceptable carriers or additives such as an excipient, and if necessary, with a binder, disintegrator, lubricant, coloring agent, taste and smell modifiers, filler, coating material or the like and then formed into tablets, granule, powder, capsules and suppositories by known methods. Here, the excipient includes saccharides, starch, inorganic excipient and plant powders; the binder includes starch paste solution, gum arabic, gelatin, polyvinyl pyrrolidone and polyvinyl alcohol; the disintegrator includes starch, agar, gelatin powder, calcium carbonate and sodium hydrogencarbonate; the lubricant includes magnesium stearate, talc, hydrogenated vegetable oils and silicone oils; and the coating material includes sugars, glues (gelatin, glycerol, sorbitol) and film coating materials.

To prepare an injection drug, compound (I) is dissolved, dispersed or emulsified in an aqueous medium such as distilled water in advance, or is made into a powder, which is dissolved in an aqueous medium upon use. As for the injection route, intravenous, intra-arterial, intra-portal, intraperitoneal, intramuscular and subcutaneous routes are mentioned.

EXAMPLES

This invention will now be explained by way of Examples, which however should not be construed as limiting the invention thereto.

EXAMPLE 1

Anti-protozoan action 1 (in vitro)

A204 cells (derived from a rhabdomyoma), which had been infected in advance with *Trypanosoma cruzi* and maintained by subculture at 37° C., were cultured in a 24-well plate for tissue culture. The protozoa in the number of about $10^5$ were confirmed to be present. After the cells were treated with 50 μmol, 100 μmol and 500 μmol of compounds 1) to 3), they were cultured at 37° C. for 24 hours. Life and death of the protozoa was observed under microscope and scored. Criteria for the scoring and the results are given below. The medium used was Dulbecco Modified Eagle Medium manufactured by Dainihon-Seiyaku K. K. added with 10% bovine serum. Control was free of any of compounds 1 to 3).

Compound 1): Compound (I), wherein
R is $-CH_2OCH_2CH=CHCH_2OH$
Compound 2): Compound (I), wherein
R is $-CH_2OCH(CH_2OH)_2$
Compound 3): Compound (I), wherein R is 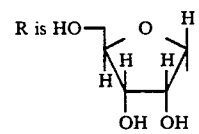

TABLE 1

| Concentration Compounds | Results | | |
| --- | --- | --- | --- |
| | 50 μmol | 100 μmol | 500 μmol |
| Compound 1) | ± | — | — |
| Compound 2) | ++ | ++ | — |
| Compound 3) | ++ | ++ | + |

Criteria for Scoring
+++: same number of protozoa alive as control
++: slightly less number alive than control
+: less number alive than control
±: only a few alive
—: all dead The above results show that compounds 1) to 3) have an excellent anti-protozoan action.

EXAMPLE 2

Anti-protozoan action 2 (in vitro)

*Trypanosoma cruzi* was cultured at 27° C. in a GIT medium (serum-free medium) manufactured by Nippon Seiyaku K. K. which was modified to contain 12.4 mol of hemine. 50 μmol, 100 μmol, 250 μmol and 500 μmol of each of compounds 1) to 3) were added thereto. 120 hours later, life or death of the protozoa was observed under microscope and scored according to the criteria in Example 1. The results are shown in Table 2. Control was free of any of compounds 1) to 3).

TABLE 2

| Concentration Compounds | 50 μmol | 100 μmol | 250 μmol | 500 μmol |
| --- | --- | --- | --- | --- |
| Compound 1) | ++ | ++ | + | — |
| Compound 2) | +++ | +++ | +++ | +++ |
| Compound 3) | +++ | +++ | +++ | + |

EXAMPLE 3

Anti-protozoan action (in vivo)

*Trypanosoma cruzi* (Tulahuen strain) in the number of 400,000 was intraperitoneally administered to a group of 4 week old male ICR mice. At each of fifth, sixth, seventh, eighth and ninth day of the administration, 200 mg/kg of compound 1) was given to the mice. Control group was given saline solution instead of compound 1). The anti-protozoan effect of compound 1) was determined based on the days of survival of the mice.

As a result, 2 mice out of 3 mice of control survived 14 days and the other 15 days, while all of 3 mice administered with compound 1) survived more than 50 days. Compound 1) was thus proved to have an excellent in vivo anti-protozoan action.

EXAMPLE 4

Anti-protozoan action (in vivo)

*Trypanosoma cruzi* (Tulahuen strain) in the number of 200,000 was intraperitoneally administered to a group of 5 week old male C3H/Hecrj mice. At each of fourth, fifth, sixth, seventh and eighth day of the administration, 200 mg/kg of compound 1) was given to the mice. Control group was given saline solution instead of compound 1). The anti-protozoan effect of compound 1) was determined based on the days of survival of the mice.

As a result, 2 mice of the control group survived 12 days while 4 mice administered with compound 1) survived more than 20 days. Compound 1) was thus proved to have excellent anti-protozoan action.

EXAMPLE 5

Five groups (Groups 1 to 5) of four week old ICR male mice, each group consisting of 3 mice, were provided. Group 2 and Group 5 mice were given 4.4 mg of acrylic acid-diisobutylvinyl ether copolymer (monomer ratio=1:1, average molecular weight=$1.29 \times 10^5$) as dissolved in a 0.2 ml saline. On the second day, all animals were intraperitoneally given *Trypanosoma cruzi* (Tulahuen Strain) in the number of 40,000 for each. On the fifth, sixth, seventh, eighth and ninth day of the administration of the Tripanosoma, Group 1 and Group 2 mice were given saline, and Group 3 and Group 5 mice were given compound 1) (200 mg/kg) as dissolved in saline. Group 4 mice were intraperitoneally given 4.4 mg of acrylic acid-diisobutyl vinyl ether copolymer (monomer ratio=1:1, average molecular weight=$1.29 \times 10^5$) and compound 1) (200 mg/kg) on the fifth day of the administration of the Trypanosoma, and on the sixth, seventh, eighth and ninth day of the administration, compound 1) (200 mg/kg) was intraperitoneally administered. Observation was continued until 60th day of administration of Trypanosoma. The mice which were alive on the 60th day were killed and dissected to check the presence or absence of the protozoa in blood, the heart and in the liver under microscope. The results are shown in Table 4.

TABLE 4

| Mice Group No. | Number of Dead Samples | Presence of Protozoa (60th day) | | |
|---|---|---|---|---|
| | | Blood | Heart | Liver |
| 1. | 1 on the 13th day of Trypanosoma Administration 1 on the 14th day of Trypanosoma | + | + | + |
| 2. | Administration 1 on the 17th day of Trypanosoma Administration 1 on the 18th day of Trypanosoma Administration | + | + | + |
| 3. | 0 | + | + | + |
| 4. | 0 | ±* | ±* | ±* |
| 5. | 0 | — | — | — |

*± means that although protozoa were observed, the number of the same was very small.

The data in Table 4 shows that there was no death in the groups (Group Nos. 3, 4 and 5) which were given compound 1), which indicates effective anti-Trypanosoma action of compound 1). Further almost no protozoa was observed in the body of the animals of the groups (Group Nos. 4 and 5) which were given compound 1) and an anionic copolymer.

EXAMPLE 6

Acute toxicity

ICR mice were intraperitoneally administered with compound 1) for the acute toxicity test. Observation was continued for 14 days after the administration. The results are shown in Table 3.

TABLE 3

| Compounds | $LD_{50}$ (mg/kg) |
|---|---|
| Compound 1) | 830 |
| Compound 2) | 4,300 |
| Compound 3) | >5,000 |

The antiprotozoal composition according to this invention has an excellent anti-protozoan action, and is very useful for the prevention or treatment of acute and chronic infectious diseases caused by various protozoa, especially *Trypanosoma cruzi*.

What is claimed is:

1. An antiprotozoal composition which is effective against the protozoan *Trypanosoma cruzi* containing a 2-nitroimidazole derivative of Formula (I):

wherein R is —CH$_2$OCH$_2$CH=CHCH$_2$OH or —CH$_2$OCH(CH$_2$OH)$_2$, and an acrylic acid-diisobutylvinyl ether copolymer.

2. A method of treatment of an infectious disease caused by the protozoan *Trypanosoma cruzi*, which comprises:

administering to a patient a therapeutically effective amount of an antiprotozoal containing as its active component a 2-nitroimidazole derivative of Formula (I):

wherein R is —CH$_2$OCH$_2$CH=CHCH$_2$OH or —CH$_2$OCH(CH$_2$OH)$_2$, and an acrylic acid-diisobutylvinyl ether copolymer.

* * * * *